United States Patent
Peevers et al.

(10) Patent No.: US 9,656,944 B2
(45) Date of Patent: May 23, 2017

(54) FATTY ACID ESTER COMPOSITIONS FOR USE AS EMOLLIENTS

(71) Applicant: CRODA INTERNATIONAL PLC, Yorkshire (GB)

(72) Inventors: Rebecca Louise Peevers, Yorkshire (GB); John Robin Latus, Yorkshire (GB); Jonathan David Townend, Yorkshire (GB)

(73) Assignee: CRODA INTERNATIONAL PLC, East Yorkshire (GB)

( * ) Notice: Subject to any disclaimer, the term of this patent is extended or adjusted under 35 U.S.C. 154(b) by 0 days.

(21) Appl. No.: 14/365,326

(22) PCT Filed: Nov. 26, 2012

(86) PCT No.: PCT/GB2012/052918
§ 371 (c)(1),
(2) Date: Jun. 13, 2014

(87) PCT Pub. No.: WO2013/093411
PCT Pub. Date: Jun. 27, 2013

(65) Prior Publication Data
US 2015/0299098 A1 Oct. 22, 2015

(30) Foreign Application Priority Data

Dec. 23, 2011 (GB) .................. 1122220.5

(51) Int. Cl.
| | | |
|---|---|---|
| *C07C 51/00* | (2006.01) | |
| *C07C 69/24* | (2006.01) | |
| *A61K 8/37* | (2006.01) | |
| *A61Q 19/00* | (2006.01) | |
| *C07C 69/26* | (2006.01) | |
| *A61K 8/06* | (2006.01) | |
| *C07C 67/08* | (2006.01) | |

(52) U.S. Cl.
CPC .............. *C07C 69/24* (2013.01); *A61K 8/062* (2013.01); *A61K 8/37* (2013.01); *A61Q 19/00* (2013.01); *A61Q 19/007* (2013.01); *A61Q 19/008* (2013.01); *C07C 67/08* (2013.01); *C07C 69/26* (2013.01)

(58) Field of Classification Search
CPC .................................................. C07C 69/24
USPC ........................................................ 554/170
See application file for complete search history.

(56) References Cited

U.S. PATENT DOCUMENTS

| | | |
|---|---|---|
| 3,536,810 A | 10/1970 | Moculeski |
| 5,578,299 A | 11/1996 | Starch |
| 2004/0063980 A1 | 4/2004 | Raths et al. |
| 2007/0154439 A1 | 7/2007 | Dorf |
| 2008/0249172 A1 | 10/2008 | Ansmann et al. |
| 2008/0287540 A1 | 11/2008 | Wright et al. |
| 2010/0209462 A1 | 8/2010 | Dierker |
| 2010/0280111 A1* | 11/2010 | Aoki ................ A61K 8/44 514/547 |
| 2012/0156271 A1 | 6/2012 | Matsuzawa et al. |
| 2014/0121394 A1 | 5/2014 | Dierker et al. |

FOREIGN PATENT DOCUMENTS

| | | |
|---|---|---|
| DE | 10 2005052173 | 5/2007 |
| EP | 2343044 | 7/2007 |
| JP | 53-1839 A | 8/1978 |
| JP | 57-006790 A | 1/1982 |
| JP | 61207313 | 9/1986 |
| JP | 8-175968 | 7/1996 |
| JP | 1999-180836 A | 7/1999 |
| JP | 2001-039815 A | 2/2001 |
| JP | 2001-510148 | 7/2001 |
| JP | 2001-516707 | 10/2001 |
| JP | 2001-520304 A | 10/2001 |
| JP | 2002-193788 A | 7/2002 |
| JP | 2003-523373 | 8/2003 |
| JP | 2003-534260 A | 11/2003 |
| JP | 2004-529084 | 9/2004 |
| JP | 2005-518389 | 6/2005 |
| JP | 2006-045145 A | 2/2006 |
| JP | 2007-504147 | 3/2007 |
| JP | 2008-127340 A | 6/2008 |
| JP | 2008-533070 | 8/2008 |
| JP | 2009-507971 | 2/2009 |
| JP | 2010-526111 | 7/2010 |
| JP | 2010-248178 A | 11/2010 |
| JP | 2010-285361 A | 12/2010 |
| JP | 2011-098926 A | 5/2011 |
| WO | WO 95/00107 | 1/1995 |
| WO | WO 99/03447 | 1/1999 |
| WO | WO 99/13847 | 3/1999 |

(Continued)

OTHER PUBLICATIONS

Ngo et al, "Synthesis and physical properties of isostearic acids and their esters", Eur. J. Lipid Sci. Technol., vol. 113, pp. 180-188, publication date Dec. 31, 2011.*
International Preliminary Report on Patentability for PCT/GB2012/052918, Issued Jun. 24, 2014.
Fragrance Journal, Feb. 1994, pp. 89-95, English Abstract Included.
Chinese Third Office Action dated Jun. 13, 2016 for Application No. 201280063829.5, including English translation, 16 pages.

(Continued)

*Primary Examiner* — Deborah D Carr
(74) *Attorney, Agent, or Firm* — RatnerPrestia

(57) ABSTRACT

A novel fatty acid ester having the general formula $R^1$—$COOR^2$ wherein $R^1$ and $R^2$ are hydrocarbon groups derived from a branched fatty acid and an alcohol, respectively. $R^1$ is derived from a branched fatty acid which has been refined from a commercially available acid to give a product with a high concentration of monobranched fatty acids and a low concentration of polybranched fatty acids. The use of the ester derived from the refined fatty acid is found to be particularly useful in personal care compositions, for example as an emollient.

15 Claims, No Drawings

(56) References Cited

FOREIGN PATENT DOCUMENTS

| WO | WO 01/62214 A1 | 8/2001 | |
|---|---|---|---|
| WO | WO 01/89466 A1 | 11/2001 | |
| WO | WO 03/055455 A1 | 7/2003 | |
| WO | WO 2005/023750 | 3/2005 | |
| WO | WO 2005/023750 A2 | 3/2005 | |
| WO | WO 2006/064685 A1 | 6/2006 | |
| WO | WO 2008/135187 A1 | 11/2008 | |
| WO | WO 2008135187 A1 * | 11/2008 | ............... A61K 8/37 |
| WO | WO 2009/054931 A2 | 4/2009 | |
| WO | WO 2011/000487 | 1/2011 | |
| WO | WO 2011/041680 | 4/2011 | |
| WO | WO 2011/052674 A1 | 5/2011 | |

OTHER PUBLICATIONS

Ngo, H.L., et al., "Synthesis and physical properties of isotearic acids and their esters," Feb. 9, 2011, pp. 180-188, vol. 113, European Journal of Lipid Science and Technology.

Goldemberg, Robert L. and De La Rosa, Consuelo P.; "Correlation of Skin Feel of Emollients to their Chemical Structure", J. Cos. Cosmet. Chem., 22, 635-654, Sep. 17, 1971.

Mantri, Kshudiram et al., "Efficient Esterification of Long Chain Aliphatic Carboxylic Acids with Alcohols Over $Z_R OCL_2$ $8H_2O$ Catalyst" Synthesis, 2005, No. 12; pp. 1939-1944.

Ieda, Noburu et al.; "Esterification of Long-Chain Acids and Alcohols Catalyzed by Ferric Chloride Hexahydrate"; Ind. Eng. Chem Res. 2008, 47, pp. 8631-8638.

Mantri, Kshudiram et al. "Esterification of Long Chain Aliphatic Acids with Long Chain Alcohols Catalyzed by Multi-Valent Metal Salts"; Chemistry Letters vol 34, No. 11 (2005) pp. 1502-1503.

Japanese Office Action with English Translation for JP 2014-548173, Issued May 10, 2016.

Roehl, E.L. et al. "Isostearic Acid and Isosteraric Acid Derivatives"; Cosmetics and Toiletries, May 1990 vol. 105, pp. 79-87.

McMahon, D.H. and Crowell, E.P.; "Characterization of Products from Clay Catalyzed Polymerization of Tall Oil Fatty Acids"; Journal of the American Oil Chemists' Society; Dec. 1974, vol. 51, pp. 522-527.

International Search Report for PCT/GB2012/052918, Issued Jan. 2, 2013.

* cited by examiner

FATTY ACID ESTER COMPOSITIONS FOR USE AS EMOLLIENTS

CROSS REFERENCE TO RELATED APPLICATIONS

This application is the U.S. National Phase application of PCT International Application No. PCT/GB2012/052918, filed Nov. 26, 2012, and claims priority of British Patent Application No. 1122220.5 filed Dec. 23, 2011, the disclosures of which are incorporated herein by reference in their entireties for all purposes.

FIELD OF THE INVENTION

The present invention relates to novel emollients, specifically novel emollients for use in personal care compositions. The novel emollients are emollients which can be used to replicate the emollient effect of naturally derived emollients.

BACKGROUND OF THE INVENTION

Many emollients used widely in personal care compositions are derived from vegetable and/or animal matter. One such example is squalane. Squalane is an emollient which can be derived from a variety of plant and animal sources. It is often used in personal care compositions as it is an effective emollient. The emollient effect, as well as the fact that the compound is stable, i.e., it is not prone to oxidation, makes squalane a desirable ingredient for use as an emollient in personal care compositions including moisturisers, dry skin treatments, oily skin treatments, anti-aging creams and eczema treatments.

Squalane is a saturated form of squalene which is found in human sebum produced in the sebaceous gland and excreted up to the skin's surface from hair follicles, and which contributes to skin waterproofing, innate immunity and elasticity. Therefore, squalane is also a useful emollient for use in personal care products for sensitive skin, because the structure of the compound is so close to that of the naturally-occurring squalane.

The supply of squalane derived from natural sources, particularly vegetable squalane, depends on the availability of the natural source. This puts a limit on the amount of naturally derived squalane available for use. A lot of naturally derived squalane is derived from olive oil. The variable supply of olive oil means that the supply of naturally derived squalane for use in personal care products is also variable, and cannot be relied on.

As a result of the supply issues with naturally derived squalane, formulators are looking to use other emollients in personal care products. However, other emollients are not as stable as squalane, and thus the products lack the effectiveness of squalane-containing products.

There exists a need for an alternative to naturally derived squalane which delivers both the same or a greater level of stability as that seen in samples of naturally-derived squalane.

Synthetically derived compositions which aim to mimic naturally occurring materials are often based on branched fatty acids, as these are often liquid at room temperature and easy to work with, without the disadvantage of being unstable. Commercially available branched fatty acids such as isostearic acid, are obtained as a by-product of the catalytic or thermal dimerisation of unsaturated straight chain fatty acids. Isostearic acid is produced by heating oleic acid in the presence of catalyst, generally clay, to produce dimer, trimer and higher oligomer acids. But instead of polymerising, a portion of the oleic acid rearranges to give a branched, monomeric fatty acid which can be isolated by distillation and hydrogenated. This saturated branched monomeric fatty acid is a mixture of various linear and mainly branched, both monobranched and polybranched, saturated acids which is known as isostearic acid.

Isostearic acid exhibits better stability to oxidation than oleic acid, and is a very useful product which is sold into a wide range of application areas including cosmetic applications.

We have discovered that monobranched fatty acids can have significant advantages over polybranched fatty acids. The prior art is silent with regards to monobranched and polybranched fatty acids, compositions containing a high concentration of monobranched fatty acids and a low concentration of polybranched fatty acids, and their use in the production of emollients.

It is an object of the present invention to address at least one of the disadvantages associated with the prior art.

DETAILED DESCRIPTION OF THE INVENTION

According to a first aspect of the present invention, there is provided a novel fatty acid ester having the general formula I:

$$R^1\text{—}COOR^2 \qquad (I)$$

wherein $R^1$ is a hydrocarbon chain having 9 to 29 carbon atoms, wherein at least 60% by weight of the molecules of formula I comprise a mono alkyl-branched $R^1$ group and less than 25% by weight of the molecules of formula I comprise a poly alkyl-branched $R^1$ group, and $R^2$ is a hydrocarbon chain comprising 2 to 16 carbon atoms.

$R^1$ is preferably present in the ester as a mixture of molecules of different isomers.

Preferably, $R^2$ has a carbon chain length shorter than that of $R^1$. In other words, the carbon chain length of $R^1$ is preferably longer than the carbon chain length of $R^2$. Preferably, $R^2$ has a carbon chain length which is at least two, preferably at least 4 and most preferably at least 6 carbon atoms shorter than that of $R^1$.

$R^1$ is preferably a saturated, branched hydrocarbon chain having 13 to 23, more preferably 15 to 21, especially 17 to 21 carbon atoms.

Preferably at least 65%, more preferably at least 70%, especially at least 75% by weight of the molecules of formula I comprise a mono alkyl-branched $R^1$ group. Preferably less than 20%, preferably less than 15%, more preferably less than 10% and especially less than 5% by weight of the molecules of formula I comprise a poly alkyl-branched $R^1$ group. The mono alkyl group is preferably positioned in the $R^1$ hydrocarbon chain away from the ester grouping, more preferably it is positioned in the middle of the $R^1$ hydrocarbon chain. By the term "middle" as used herein, it is meant in a position in the hydrocarbon chain approximately half way between the ester grouping and the terminal carbon of the hydrocarbon chain.

The mono alkyl branching is preferably a lower alkyl branching. The lower alkyl branching may be $C_1$ to $C_6$ branching, preferably methyl, ethyl, propyl or a mixture thereof. Preferably, the monoalkyl branching is at least 80% methyl, more preferably at least 90% and especially at least 95% methyl branching.

Preferably, the novel fatty acid ester is produced from the esterification reaction of a refined, branched fatty monocarboxylic acid and an alcohol, wherein $R^1$ in formula I results from the refined, branched fatty acid and $R^2$ in formula I results from the alcohol. Preferably, the refined, branched fatty monocarboxylic acid has the general formula $R^1COOH$. Preferably, the alcohol has the general formula $R^2OH$. Preferably, the refined, branched fatty acid is refined from a commercially available source of branched fatty monocarboxylic acid.

Preferably, the branched fatty acid ester of formula I is fully saturated. Examples of suitable branched primary fatty acid esters include, but are not limited to, isostearate esters derived from highly-refined isostearic acid, wherein at least 60% by weight of the isostearic acid molecules are mono alkyl branched and less than 25% by weight of the isostearic acid molecules are poly alkyl branched; isobehenate esters derived from highly-refined isobehenic acid, wherein at least 60% by weight of the isobehenic acid molecules are mono alkyl branched and less than 25% by weight of the isobehenic acid molecules are poly alkyl branched.

An especially preferred branched, primary, fatty acid ester of formula I is derived from the reaction of isostearic acid, wherein at least 60% by weight of the isostearic acid molecules are mono alkyl branched and less than 25% by weight of the isostearic acid molecules are poly alkyl branched, with an alcohol.

In the refined, branched monocarboxylic acid starting material for the ester, preferably at least 65%, more preferably at least 70%, especially at least 75% by weight of the monocarboxylic acid molecules are mono alkyl branched. Preferably, less than 20%, preferably less than 15%, more preferably less than 10% and especially less than 5% of the monocarboxylic acid molecules are poly alkyl branched.

The mono alkyl group in the carboxylic acid is preferably positioned towards the middle of the hydrocarbon chain. For the branched monocarboxylic acid, $R^1COOH$, $R^1$ preferably has 13 to 23, more preferably 15 to 21 and especially 17 to 21 carbon atoms.

The remaining molecules in the refined, branched monocarboxylic acid are preferably linear acids and/or lactone species. Preferably, less than 20%, preferably less than 17%, more preferably less than 12% and especially less than 10% of the monocarboxylic acid molecules are linear acids. Preferably, less than 20%, preferably less than 17%, more preferably less than 12% and especially less than 10% of the monocarboxylic acid molecules are lactone species. Preferably, the refined, branched monocarboxylic acid comprises (i) greater than 60% by weight of monobranched $C_{10}$-$C_{26}$ fatty acids or alkyl esters thereof, (ii) less than 25% by weight of polybranched $C_{10}$-$C_{26}$ fatty acids or alkyl esters thereof, (iii) less than 10% by weight of linear $C_{10}$-$C_{26}$ fatty acids or alkyl esters thereof, and (iv) less than 10% by weight of lactones, all based on the total weight of the branched monocarboxylic acid. More preferably, the refined, branched monocarboxylic acid comprises (i) greater than 70% by weight of monobranched $C_{10}$-$C_{26}$ fatty acids or alkyl esters thereof, (ii) less than 10% by weight of polybranched $C_{10}$-$C_{26}$ fatty acids or alkyl esters thereof, (iii) less than 10% by weight of linear $C_{10}$-$C_{26}$ fatty acids or alkyl esters thereof, and (iv) less than 10% by weight of lactones, all based on the total weight of the branched monocarboxylic acid.

The refined, saturated branched fatty acid, $R^1COOH$, may be obtained by refining standard, commercial, corresponding saturated branched fatty acids, $R^3COOH$, where $R^3$ has 11 to 23 carbon atoms, and typically 40% by weight of the $R^3COOH$ molecules are mono alkyl branched and 31% by weight of the $R^3COOH$ are poly alkyl branched (based on GC analysis). The commercial saturated, branched fatty acids, $R^3COOH$, are preferably manufactured as a by-product of the polymerisation of the naturally occurring corresponding unsaturated fatty acid, $R^4COOH$ to produce dimer/trimer acid. Heating the naturally occurring unsaturated fatty acid, where $R^4$ has 11 to 23 carbon atoms, in the presence of certain catalysts produces dimeric, trimeric and higher polymeric products. Instead of polymerising, a portion of the naturally occurring unsaturated fatty acid rearranges to give a branched, monomeric fatty acid which can be isolated by distillation and then hydrogenated. The saturated branched, monomeric fatty acid product, $R^3COOH$ is a mixture of various linear and mainly branched, both mono- and poly-branched, saturated acids.

A further possible route to $R^3COOH$ from $R^4COOH$ uses a zeolite catalyst, for example, Ferrierite, of small pore diameter which restricts formation of the dimeric, trimeric and higher polymeric products in favour of the rearrangement reaction leading to the branched monomeric fatty acid which can be isolated by distillation and then hydrogenated.

Other routes to saturated branched fatty acids, $R^3COOH$, include hydroformylation of the corresponding alkene followed by oxidation of the resulting aldehyde. Also, specifically for when $R^3$ is a hydrocarbon chain of 17 carbon atoms, one commercial route is dimerisation of the corresponding $C_9$ alcohol to isostearyl alcohol which is then oxidised to the corresponding isostearic acid.

The commercially obtained $R^3COOH$ can be refined in a variety of ways, for example clathration, distillation, fractional crystallisation and chromatography.

One preferred method of refining is a clathration process with urea and a lower alcohol. This clathration refining process may be carried out in the following way. Commercial non-refined saturated, branched fatty acid having 12 to 24 carbon atoms is dissolved in a mixture of urea and a lower alcohol and refluxed at 65-90° C., especially 80-85° C. for 1 to 2 hours. The lower alcohol preferably has 1 to 4 carbon atoms and especially preferred examples are methanol and ethanol because of the ease of their subsequent removal from the reaction mixture. The weight ratio of commercial non-refined saturated, branched fatty acid having 12 to 24 carbon atoms to urea may be from 7:1 to 1:7, preferably 5:1 to 1:5 and more preferably 2:1 to 1:2. The weight ratio of urea to lower alcohol may be from 10:1 to 1:10, preferably from 5:1 to 1:5 and especially from 1:1 to 1:2. The clear solution formed during reflux is allowed to cool to ambient temperature or is refrigerated until crystals of a urea clathrate are formed. The urea clathrate is separated either by filtering or centrifugation and the filtrate can be isolated, provided at least 60% by weight of the acid molecules are mono alkyl branched, and less than 25% by weight of the acid molecules are poly alkyl branched.

However, the filtrate may be further mixed with urea and the lower alcohol and refluxed at 65-90° C., especially 80-85° C. for a further 1 to 2 hours in a second clathration process. The weight ratio of urea to lower alcohol for this second clathration process may be from 3:1 to 1:8, preferably from 2:1 to 1:5 and especially from 2:1 to 1:2. The clear solution formed during reflux is allowed to cool to ambient temperature or is refrigerated until crystals of a second urea clathrate are formed. This second urea clathrate is separated off and may be placed in a brine solution and heated in an oven until all of the second urea clathrate has dissolved. The refined, saturated, branched fatty acid having 12 to 24 carbon atoms, wherein at least 60% by weight of the acid molecules are mono alkyl branched and less than 25% by weight of the acid molecules are poly alkyl branched, separates from the brine solution and can be isolated.

Alternatively the second filtrate may be mixed with urea and the clathration process undertaken for a third time before the refined, saturated, branched fatty acid having 12 to 24 carbon atoms, wherein at least 60% by weight of the acid molecules are monoalkyl branched and less than 25% by weight of the acid molecules are polyalkyl branched is obtained.

Preferably, where a clathration process is used to prepare the refined, monobranched fatty acid, the process is undertaken as a single step process, i.e. the process is terminated once the first urea clathrate is produced.

The clathration process may also be undertaken where urea is replaced by thiourea.

Additional alternative methods may be employed to obtain the refined, highly monobranched fatty acid.

Preferably the refined, saturated, branched fatty acid, $R^1COOH$ has $R^1$ having 13 to 23 carbon atoms, more preferably 15 to 21 carbon atoms and especially 17 to 21 carbon atoms. Examples include refined isostearic acid and refined isobehenic acid.

$R^2$ is preferably a saturated hydrocarbon chain having 4 to 14, more preferably 6 to 12, especially 8 to 10 carbon atoms. $R^2$ is preferably a linear hydrocarbon chain.

The alcohol starting material for the ester is preferably a linear alcohol, preferably a primary alcohol. The alcohol preferably has a carbon chain length of 4 to 14, more preferably 6 to 12, especially 8 to 10 carbon atoms. Examples of suitable alcohols include, but are not limited to, hexyl alcohol, octyl alcohol, decyl alcohol and dodecyl alcohol, preferably octyl alcohol or decyl alcohol.

The branched, fatty acid ester of formula I has been found to be of use as an emollient, particularly as a synthetic alternative to squalane, in personal care compositions.

Therefore, according to a second aspect of the present invention, there is provided a novel emollient comprising an ester of a refined, fatty alkyl-branched carboxylic acid and an alcohol, wherein the refined carboxylic acid comprises at least 60% by weight mono alkyl-branched carboxylic acid and less than 25% by weight poly alkyl-branched carboxylic acid.

Preferably, the alcohol has a carbon chain length which is shorter than that of the branched carboxylic acid. Preferably, the alcohol has a carbon chain length which is at least two, preferably at least 4 and most preferably at least 6 carbon atoms shorter than that of the branched carboxylic acid.

Preferably, the refined, alkyl branched carboxylic acid is a saturated fatty acid. Preferably, the refined, alkyl branched carboxylic acid is a $C_{10}$ to $C_{30}$ fatty acid.

Preferably, the alcohol is a linear alcohol. Preferably, the alcohol is a saturated alcohol. Preferably, the alcohol has a carbon chain of $C_2$ to $C_{16}$, preferably $C_4$ to $C_{14}$, more preferably $C_6$ to $C_{12}$, and most preferably $C_8$ to $C_{10}$.

The emollients of the present invention are suitable for use as emollients in personal care compositions, particularly in oil in water emulsions; water in oil emulsions; anhydrous formulations including lipsticks, eye shadows, baby oils, massage oils and the like; gel-based formulations and detergent formulations; more particularly in personal care emulsion compositions such as oil in water emulsions. Personal care emulsion compositions can take the form of creams, liquids and milks desirably, and typically include emollients to provide a good skinfeel. Typically, personal care emulsion products use emollients in amounts of about 1 to about 40% by weight, more preferably 5 to 35% and most preferably 10 to 30% by weight of the emulsion.

The esters/emollients of the invention may also be combined with other emollients in oil in water emulsions. Any additional emollients in the emulsion of the present invention will preferably mainly be an emollient oil of the type used in personal care or cosmetic products. The emollient can and usually will be an oily material which is liquid at ambient temperature. Alternatively it can be solid at ambient temperature, in which case in bulk it will usually be a waxy solid, provided it is liquid at an elevated temperature at which it can be included in and emulsified in the composition. The manufacture of the composition preferably uses temperatures up to 100° C., more preferably about 80° C., and therefore such solid emollients will preferably have melting temperatures of less than 100° C., and more preferably less than 70° C.

Suitable normally liquid emollient oils include non-polar oils, for example mineral or paraffin, especially isoparaffin, oils, such as that sold by Croda as ARLAMOL™ HD; or medium polarity oils, for example vegetable ester oils such as jojoba oil, vegetable glyceride oils, animal glyceride oils, such as that sold by Croda as CRODAMOL™ GTCC (caprylic/capric triglyceride), synthetic oils, for example synthetic ester oils, such as isopropyl palmitate and those sold by Croda as CRODAMOL™ IPM and CRODAMOL™ DOA, ether oils, particularly of two fatty e.g. C8 to C18 alkyl residues, such as that sold by Cognis as CETIOL® OE (dicapryl ether), guerbet alcohols such as that sold by Cognis as EUTANOL® G (octyl dodecanol), or silicone oils, such as dimethicone oil such as those sold by Dow Corning as DC200, cyclomethicone oil, or silicones having polyoxyalkylene side chains to improve their hydrophilicity; or highly polar oils including alkoxylate emollients for example fatty alcohol propoxylates such as that sold by Croda as ARLAMOL™ PS15 (propoxylated stearyl alcohol).

Suitable emollient materials that can be solid at ambient temperature but liquid at temperatures typically used to make the compositions of this invention include jojoba wax, tallow and coconut wax/oil. In some cases solid emollients may dissolve wholly or partly in liquid emollients or in combination the freezing point of the mixture may be suitably low. Where the emollient composition is a solid (such as fatty alcohols) at ambient temperature, the resulting dispersion may technically not be an emulsion (although in most cases the precise phase of the oily disperse phase cannot readily be determined) but such dispersions behave as if they were true emulsions and the term emulsion is used herein to include such compositions.

The end use formulations of such compositions include, in the field of personal care products, moisturizers, sunscreens, after sun products, body butters, gel creams, high perfume containing products, perfume creams, baby care products including baby oils, hair conditioners, hair relaxer formulations, skin toning and skin whitening products, water-free products, anti-perspirant and deodorant products, tanning products, cleansers, 2-in-1 foaming emulsions, multiple emulsions, preservative free products, emulsifier free products, mild formulations, scrub formulations, e.g., containing solid beads, silicone in water formulations, pigment containing products, sprayable emulsions, colour cosmetics, conditioners, shower products, foaming emulsions, make-up remover, eye make-up remover, and wipes.

Such formulations include green formulations, natural formulations and naturally certified formulations.

Personal care emulsion compositions comprising these emollients may include various other personal care ingredients. For example, suitable other ingredients include one or more ingredients such as cleansing agents, hair conditioning agents, skin conditioning agents, hair styling agents, anti-dandruff agents, hair growth promoters, perfumes, sunscreen compounds, pigments, moisturizers, film formers, humectants, alpha-hydroxy acids, hair colours, make-up agents, detergents, thickening agents, antiseptic agents, deodorant actives and surfactants.

According to a third aspect the present invention, there is provided the use of a branched, fatty acid ester of general formula I:

$$R^1—COOR^2 \qquad (I)$$

wherein $R^1$ is a hydrocarbon chain having 9 to 29 carbon atoms, wherein at least 60% by weight of the molecules of formula I comprise a mono alkyl-branched $R^1$ group and less than 25% by weight of the molecules of formula I comprise a poly alkyl-branched $R^1$ group, and $R^2$ is a hydrocarbon chain comprising 2 to 16 carbon atoms, as an emollient.

According to a fourth aspect of the present invention, there is provided the use of a branched, fatty acid ester of general formula I:

$$R^1—COOR^2 \qquad (I)$$

wherein $R^1$ is a hydrocarbon chain having 9 to 29 carbon atoms, wherein at least 60% by weight of the molecules of formula I comprise a mono alkyl-branched $R^1$ group and less than 25% by weight of the molecules of formula I comprise a poly alkyl-branched $R^1$ group, and $R^2$ is a hydrocarbon chain comprising 2 to 16 carbon atoms, as synthetic alternative to squalane.

Preferably, the fatty acid ester of the third and/or fourth aspect of the invention is used as an emollient and/or synthetic squalane alternative in a personal care composition.

Any of the above-described features of the invention may be taken in any combination, and/or with any aspect of the invention.

The invention will now be illustrated in more detail, by way of example only, with reference to the accompanying tables, in the following non-limiting examples.

Example 1

Preparation of isostearic acid, wherein at least 60% by weight of the acid molecules have monoalkyl branches and less than 25% by weight of the acid molecules have polyalkyl branches by a two stage clathration process.

Commercial Isostearic acid (500 g, PRISORINE™ 3505 ex Croda Europe Ltd) and Urea prills (500 g) were refluxed in methanol (2500 ml) for 2 hours. The solution was allowed to cool and then placed in a fridge (~4° C.) or allowed to cool to between 20-25° C. over night (~18 hours). Urea crystals that formed were filtered off and placed in a conical flask with brine solution. This was placed in an oven (80° C.) and stirred occasionally until all of the urea had dissolved. The resulting fatty material was pipetted off the top of the brine and labelled U1.

Urea prills (500 g) were added to the filtrate and refluxed again for 2 hours before being allowed to cool to ambient temperature or being left in the fridge overnight. The urea crystals that formed were again filtered off and the urea was dissolved as before. The resulting fatty material was labelled U2.

The methanol was removed from the filtrate and the resulting slurry was washed with warm brine solution to remove the remaining urea. The resulting fatty material was labelled Filtrate. All three fractions were dried using either sodium or magnesium sulphate.

Table 1 below illustrates the rough weights and yields (by weight) for each of the fractions.

TABLE 1

| Fraction | Weight in g | % Yield |
|---|---|---|
| U1 | 120 | 24 |
| U2 | 88 | 18 |
| Filtrate | 272 | 54 |
| Losses | 20 | 4 |

Table 2 below shows the percentage of each of the main components of standard commercial isostearic acid in each fraction as determined by gas chromatographic (GC) analysis.

TABLE 2

| | Approximate GC Areas (%) | | |
|---|---|---|---|
| Fraction | Palmitic | Mono Alkyl Branched | Poly Alkyl Branched |
| U1 | 24 | 51 | 2 |
| U2 | 1 | 86 | 4 |
| Filtrate | 2 | 5 | 65+ |
| Commercial Isostearic Acid (Comparative) | 7 | 40 | 31 |

With the percentage for poly alkyl branched material it is unclear exactly how much is the poly alkyl branched material and how much of it is other species. The quoted percentage is for material that is definitely poly alkyl branched material.

U2 is the refined branched saturated monocarboxylic acid of the invention wherein at least 60% by weight of the acid molecules have monoalkyl branches and less than 25% by weight of the acid molecules have polyalkyl branches.

Example 2

Preparation of isostearic acid, wherein at least 60% by weight of the acid molecules have monoalkyl branches and less than 25% by weight of the acid molecules have polyalkyl branches by a one stage clathration process.

Commercial Isostearic acid (PRISORINE™ 3505 ex Croda Europe Ltd (300 g)), Urea prills (500 g) and IMS/water (95/5 w/w; 769 g) were placed in a flask equipped with mantle, MC810 temperature feed-back loop, agitator and vertically configured water cooled condenser. The mixture was refluxed for 1 hour then allowed to fully crystallise, before filtering (Whatman 54, vacuum). The cake, retained in the filter funnel, was washed with 200 cm³ of IMS and allowed to drain. The washed cake was transferred to a separating funnel and washed with 2% aqueous brine at 80° C., draining off the aqueous layer after it had separated out. The wash was repeated, then the organic layer was dried over anhydrous sodium sulphate and filtered (Whatman 54, vacuum). The resulting monomethyl isostearic acid was weighed and analysed by GC.

For mass balance and analytical purposes the ethanol was removed from the filtrate and the clathration filtrate was washed twice with 2% brine (80° C.) and dried over anhydrous sodium sulphate. The resulting polybranched isostearic acid was weighed and analysed by GC.

Approximate Yields:
Monomethyl fraction: 34.7% wt
Polybranched fraction: 65.3% wt Table 3 below shows the percentage of each of the main components of standard commercial isostearic acid in each fraction as determined by gas chromatographic (GC) analysis.

TABLE 3

| Fatty acid/fatty acid type | % weight (by GC analysis) | |
|---|---|---|
| | Monobranched fraction | Polybranched fraction |
| C14:0 Myristic | 0.5 | Zero |
| C16:0 Palmitic | 8.5 | Zero |
| C18:0 Stearic | 1.9 | Zero |
| C18:0 monomethyl | 74.4 | 18.1 |
| C18:0 polybranched | 6.6 | 69.1 |
| Lactones/others | 8.1 | 12.8 |
| Total | 100.0 | 100.0 |

Example 3

Preparation of the Decyl Ester of Monobranched Fraction from Example 2

The monobranched isostearic acid clathration fraction obtained from Example 2 above, n-decyl alcohol (20-100% molar excess) and activated carbon (0.3% wt on charge size) were charged to a 500 cm$^3$ reaction vessel equipped with temperature feedback loop, nitrogen headspace purge, Dean+Stark binary separator, Vigreux fractionating column (ca. 8" depth of packing) and condenser arranged for reflux return to the column.

The reaction mixture was heated incrementally to 225° C. under nitrogen purge to reduce the acid value and then vacuum applied, gradually working up to maximum available to strip out excess unreacted alcohol. The vacuum was broken with nitrogen and the crude product filtered.

The properties of the reaction product are recorded in Table 4 below.

TABLE 4

| Parameter/units (method) | Decyl isostearate |
|---|---|
| Acid value/mgKOH/g (CUFA3) | 0.1 |
| Hydroxyl value/mgKOH/g (G1201) | zero |
| Appearance | Near water white oil |
| Odour | Slight |
| Cloud point/° C. (CUFA2) | 9° C. |

Example 4

Analysis of Skinfeel Attributes of Emollients

The emollients detailed in Table 5 were tested for their skinfeel attributes at rub out, t=0 (immediate afterfeel) and t=20 minutes afterfeel. The tests were performed by Sensory Spectrum Inc. on the emollient samples prepared by Croda International plc.

TABLE 5

| Emollient Name | Emollient Composition |
|---|---|
| E1 | Ester of Example 3 |
| E2 | 70% E1; 30% commercially available isostearyl isostearate |
| Comp | Squalane |

The tests were carried out on eleven volunteers, each trained in skinfeel descriptive analysis method. The method was repeated for each emollient.

A skin scribe was used to make a 2" diameter circle on the inner surface of the forearm. Using an automatic pipette, 0.05 cc of emollient was delivered onto the skin in the centre of the circle. The emollient was spread out within the circle using the index of middle finger in a gentle circular motion at a stroke, or rub, rate of two strokes per second.

An initial rub-out analysis was then performed as follows.

After three rubs, the wetness (amount of water perceived while spreading—from none to high amount) and spreadability (ease of moving product over the skin—from difficult/drag to easy/slip) of each of the emollients was measured.

After 12 rubs, the thickness (amount of product felt between fingertip and skin—from thin/almost no product to thick/lots of product) of each of the emollients was measured.

After 15 to 20 rubs, the perception of the amount of oil, wax and grease in the product (from none to extreme) was measured for each emollient.

Finally, at up to a maximum of 120 rubs, the absorbency was measured. This was the number of rubs at which the product lost a wet, moist feel and a resistance to continue rubbing was perceived.

An afterfeel analysis was then undertaken. The forearm was visually evaluated for the gloss of the product, i.e., the amount of light reflected off the skin surface. The stickiness of the product was measured by tapping a cleansed finger lightly over the application site to determine the degree to which the finger adhered to any residual product on the skin.

A cleansed finger was then stroked lightly across the skin once or twice to evaluate for slipperiness (ease of moving finger across the skin), thickness of residue (amount of product residue felt between the finger and the skin) and type of residue (oily, waxy, greasy, silicone, etc. and % of total residue).

The afterfeel analysis was carried out immediately after the initial rubbing tests and again after 20 minutes. The results are shown in Table 6 below.

The results are given in arbitrary units unless stated otherwise.

The results show a good correlation between emollients E1 and E2 with Comp. Therefore, it can be seen that E1 and E2 both provide an effective alternative to naturally-derived squalane. This can be seen clearly in the important measurement of the amount of residue at 20 minutes post application of each product. This measurement corresponds directly to the absorbance of the product, and shows that E1 and E2 both provide analogous absorbance results to naturally-derived squalane.

Therefore, it can be concluded that the esters of the present invention provide a novel emollient which is readily substitutable for naturally-derived squalane having analogous attributes as the tested squalane emollient.

TABLE 6

| Descriptive Attribute | E1 | E2 | Comp |
|---|---|---|---|
| Rub Out | | | |
| Spreadability | 96.3 | 96.3 | 94.9 |
| Thickness | 7.5 | 7.6 | 8.7 |
| Oil | 97 | 96 | 97.4 |
| Wax | 0 | 0.2 | 0.1 |
| Grease | 1.5 | 1.5 | 1 |
| Absorbency | 117.9 | 117.1 | 116.1 |

TABLE 6-continued

| Descriptive Attribute | E1 | E2 | Comp |
|---|---|---|---|
| Immediate Afterfeel | | | |
| Gloss | 91.2 | 96.3 | 95.6 |
| Thickness of Residue | 11.4 | 12.2 | 13.7 |
| Amount of Residue | 75.1 | 79.6 | 80.5 |
| Oily % | 79.3 | 79.3 | 76.5 |
| Wax % | 0 | 0.5 | 1.5 |
| Grease % | 5.3 | 4.3 | 7 |
| Silicone % | 15.5 | 16 | 15 |
| 20 Minute Afterfeel | | | |
| Gloss | 23.7 | 25.8 | 27.5 |
| Thickness of Residue | 6.1 | 6.2 | 7 |
| Amount of Residue | 22.9 | 29.3 | 25 |
| Oily % | 30.8 | 46.3 | 41.5 |
| Wax % | 21.5 | 13.3 | 15 |
| Grease % | 5.3 | 9.3 | 16.3 |
| Silicone % | 42.5 | 31.3 | 27.3 |

Example 5

Analysis of Skinfeel Attributes of Emulsions

The tests of Example 4 were repeated using emulsions that were formulated using the emollients described in the examples above.

The tested emulsions were formulated as per below.

| Phase A | % wt |
|---|---|
| Water | 89.00 |
| VERSAFLEX ™ V-150 (Steareth-100, Steareth-2, Mannan Gum and Xanthan Gum) | 1.00 |

| Phase B | % wt |
|---|---|
| Tested emollient* | 10.00 |

Procedure:

The phase A ingredients were combined and allowed to mix with propeller agitation until completely hydrated. Phase A was then homogenised, and Phase B was slowly added under homogenisation. After homogenisation, the emulsion was slowly stirred for several minutes to produce the resulting emulsion.

In Emulsion 1, the tested emollient was E2 from Example 4. In Emulsion A (Comparative) the tested emollient was Comp from Example 4.

The results of the analysis carried out on the skinfeel attributes of the emulsions immediately after the initial rubbing tests and again after 20 minutes are given below in Table 7.

Again, the results of the testing on the emulsions show that emollient E2 provides an effective alternative to naturally-derived squalane in formulation as well as on its own. This can be clearly seen in the important measure of the amount of residue at 20 minutes post application of each emulsion. This measurement corresponds directly to the absorbance of the emollients after evaporation of the water, and shows that emollient E2 provides an analogous absorbency to that of naturally-derived squalane.

Therefore, it can be concluded that the esters of the present invention provide novel emollients which are readily formulatable into personal care compositions and substitutable for naturally-derived squalane in personal care compositions to provide a composition that will have analogous attributes as the original squalane-containing compositions.

TABLE 7

| Descriptive Attribute | Emulsion 1 | Emulsion A (comparative) |
|---|---|---|
| Rub Out | | |
| Spreadability | 82.9 | 83.5 |
| Thickness | 9.6 | 9.6 |
| Oil | 22.6 | 24.5 |
| Wax | 3.1 | 2.8 |
| Grease | 18.7 | 19.2 |
| Absorbency | 70.2 | 70.9 |
| Immediate Afterfeel | | |
| Gloss | 23.9 | 25.1 |
| Thickness of Residue | 9.8 | 10.2 |
| Amount of Residue | 14.0 | 14.6 |
| Oily % | 14.8 | 9.0 |
| Wax % | 55.7 | 60.0 |
| Grease % | 13.8 | 18.3 |
| Silicone % | 15.7 | 12.6 |
| 20 Minute Afterfeel | | |
| Gloss | 11.5 | 11.5 |
| Thickness of Residue | 3.7 | 4.0 |
| Amount of Residue | 5.9 | 5.8 |
| Oily % | 4.0 | 4.3 |
| Wax % | 68.5 | 68.5 |
| Grease % | 4.5 | 5.8 |
| Silicone % | 23.0 | 21.5 |

Any or all of the disclosed features, and/or any or all of the steps of any method or process described, may be combined in any combination.

Each feature disclosed herein may be replaced by alternative features serving the same, equivalent or similar purpose. Therefore, each feature disclosed is one example only of a generic series of equivalent or similar features.

The above statements apply unless expressly stated otherwise. The term specification, for these purposes, includes the description and any accompanying claims, abstract and drawings.

The invention claimed is:

1. A fatty add ester mixture wherein the fatty acid esters have the general formula I:

$$R^1\text{—COOR}^2 \qquad (I)$$

wherein $R^1$ is a mixture of hydrocarbon chains having 9 to 29 carbon atoms, wherein at least 60% by weight of the molecules of formula I comprise a mono alkyl-branched $R^1$ group and less than 25% by weight of the molecules of formula I comprise a poly alkyl-branched $R^1$ group, and $R^2$ is a hydrocarbon chain comprising 2 to 16 carbon atoms, wherein the fatty acid ester mixture comprises molecules of formula I comprising a mono alkyl-branched $R^1$ group and molecules of formula I comprising a poly alkyl-branched $R^1$ group are present in the fatty acid ester mixture.

2. The fatty acid ester mixture according to claim 1, wherein the ester is produced from the esterification reaction of a refined, branched fatty monocarboxylic acid and an alcohol.

3. The fatty acid ester mixture according to claim 1, wherein $R^1$ in formula I results from a refined, branched fatty acid and $R^2$ in formula results from an alcohol.

4. The fatty acid ester mixture according to claim 1, wherein the carbon chain length of $R^1$ is longer than the carbon chain length of $R^2$.

5. The fatty acid ester mixture according to claim 1, wherein the mono alkyl branching is a lower alkyl branching.

6. The fatty acid ester mixture according to claim 1, wherein the branched fatty acid ester of formula I is fully saturated.

7. The fatty acid ester mixture according to claim 2, wherein in the refined, branched fatty monocarboxylic acid, at least 65% by weight of the monocarboxylic acid molecules are mono alkyl branched based on the total weight of the refined, branched fatty monocarboxylic acid.

8. The fatty acid ester mixture according to claim 2, wherein the refined, branched fatty monocarboxylic acid comprises:
    (i) greater than 60% by weight of monobranched $C_{10}$-$C_{26}$ fatty acids or alkyl esters thereof,
    (ii) less than 25% by weight of polybranched $C_{10}$-$C_{26}$ fatty acids or alkyl esters thereof,
    (iii) less than 10% by weight of linear $C_{10}$-$C_{26}$ fatty acids or alkyl esters thereof, and
    (iv) less than 10% by weight of lactones, all based on the total weight of the refined, branched fatty monocarboxylic acid.

9. The fatty acid ester mixture according to claim 2, wherein the refined, branched fatty monocarboxylic acid is refined from a commercially available branched fatty monocarboxylic acid.

10. The fatty acid ester mixture according to claim 1, wherein $R^2$ is a saturated hydrocarbon chain having 4 to 14 carbon atoms.

11. The fatty acid ester mixture according to claim 2, wherein the alcohol is a primary alcohol.

12. An emollient comprising an ester mixture of a refined, fatty alkyl-branched carboxylic acid and an alcohol, wherein the refined carboxylic acid comprises a mono alkyl-branched carboxylic acid and a poly alkyl-branched carboxylic acid and the refined carboxylic acid comprises at least 60% by weight mono alkyl-branched carboxylic acid and less than 25% by weight poly alkyl-branched carboxylic acid.

13. The emollient of claim 12, wherein the alcohol has a carbon chain length which is shorter than that of the refined, fatty alkyl-branched carboxylic acid.

14. A method of preparing a branched, fatty acid ester mixture of general formula I:

$$R^1\text{—}COOR^2 \qquad (I)$$

wherein $R^1$ is a mixture of hydrocarbon chains having 9 to 29 carbon atoms, wherein at least 60% by weight of the molecules of formula I comprise a mono alkyl-branched $R^1$ group and less than 25% by weight of the molecules of formula I comprise a poly alkyl-branched $R^1$ group, and $R^2$ is a hydrocarbon chain comprising 2 to 16 carbon atoms, comprising:
reacting a refined, branched fatty acid and an alcohol.

15. The method of claim 14, wherein the refined, branched fatty acid comprises a compound of formula $R^1COOH$ and the alcohol comprises a compound of formula $R^2OH$.

* * * * *